United States Patent [19]

Bakale et al.

[11] 4,224,566
[45] Sep. 23, 1980

[54] PULSED ELECTRON ATTACHMENT CONDUCTIVITY DETECTOR AND CARCINOGEN MONITOR FOR LIQUID CHROMATOGRAPHY

[76] Inventors: George Bakale, 2169 Rexwood Rd., Cleveland Heights, Ohio 44118; Earle C. Gregg, 328 N. Main St., Chagrin Falls, Ohio 44022

[21] Appl. No.: 773,831

[22] Filed: Mar. 3, 1977

[51] Int. Cl.$^3$ .......................................... G01N 27/00
[52] U.S. Cl. .................................. 324/71 R; 324/459
[58] Field of Search ............... 324/71 R, 33, 466, 459; 73/61.1 C; 23/253 R; 422/70; 210/31 C

[56] References Cited

U.S. PATENT DOCUMENTS

| | | | |
|---|---|---|---|
| 3,247,375 | 4/1966 | Lovelock | 324/33 |
| 3,634,754 | 1/1972 | Lovelock et al. | 324/33 |

OTHER PUBLICATIONS

Lovelock et al., Electron Capture Ionization Detector; Gas Chromatography, Academic Press, NY & London, 1962; pp. 219-229.

*Primary Examiner*—Michael J. Tokar
*Attorney, Agent, or Firm*—Fay & Sharpe

[57] ABSTRACT

This is a highly sensitive detection system to be used in conjunction with liquid chromatography to determine the extremely fast rates of electron attachment to electrophilic compounds in nonpolar solvents. The system integrates pulse radiolysis, liquid state electronics and liquid chromatography and is designated Pulsed Electron Attachment Conductivity-Liquid Chromatography or PEAC-LC. The detector system is responsive only to electrophilic compounds. Since electrophilicity has been correlated with carcinogenicity, the PEAC-LC detector system is a primary screening monitor for carcinogens.

10 Claims, 5 Drawing Figures

PULSED ELECTRON ATTACHMENT CONDUCTIVITY DETECTOR AND CARCINOGEN MONITOR FOR LIQUID CHROMATOGRAPHY

BACKGROUND OF THE INVENTION

Liquid Chromatography

The growth of high pressure liquid chromatography (HPLC) is the best indication of the applicability of this technique to a myriad of analytical problems. Concomitant with this growth has been the development of a wide variety of sample preparation and introduction techniques, an increase in the sensitivity and selectivity of detectors and the use of more efficient column packings which has resulted in marked reductions of analysis times. These advances in HPLC have been described by Knox[1].

1. J. H. Knox, "High Speed Liquid Chromatography", Ann. Rev. Phys. Chem. 24, 29 (1973).

Electron Attachment Rates

Occurring simultaneously with this growth of HPLC has been the characterization of the physical properties of quasifree electrons in a wide variety of nonpolar liquids in which the electron mobility, $u_e$, ranges from $<10^{-3}$ to $>10^3$ cm$^2$/volt sec.[2,3] Of these liquids, argon and xenon have been used in radiation detectors such as proportional counters [4] and gamma-cameras [5] to enhance the sensitivity of these devices due to the liquids' high stopping power of ionizing radiation. In addition, the high mobility of the electrons produced in ionizing events in these liquids increases the sensitivity of these devices since the external current is proportional to the mobilities of the radiolytic charge-carriers. Thus, an electron drifting in an electric field in a liquid xenon-filled ion chamber induces $\sim 10^7$ times more current in the external circuit than an ion drifting in the same field but in a polar liquid.

2. G. Bakale, W. Tauchert and W. F. Schmidt, "Electron Transport in Mixture of Liquid Methane and Ethane", J. Chem. Phys. 63, 4470 (1975).
3. U. Sowada, G. Bakale, K. Yoshino and W. F. Schmidt, "Electrical Field Effect on Electron Capture by SF$_6$ in Liquid Argon and Xenon", Chem. Phys. Lett. 34, 466 (1975).
4. R. A. Muller, S. E. Derenzo, G. Smadja, D. B. Smith, R. G. Smits, H. Zaklad and L. W. Alvarez, "Liquid-Filled Proportional Counter", Phys. Rev. Lett. 27, 532 (1971).
5. H. Zaklad, S. E. Derenzo, R. A. Muller and R. G. Smits, "Initial Images from a 24-Wire Liquid Xenon $\gamma$-Camera", IEEE Trans. Nuc. Sci. NS-20, 429 (1973).

The rate constants of electron attachment in these "high mobility" liquids have also been measured and found to be $>10^{14} M^{-1}$ Sec$^{-1}$, which is $\sim 10^4$ times faster than diffusion-controlled radical-radical reactions in the liquid phase. [6] These extremely high rate constants of electron attachment combined with electron mobilities orders of magnitude greater than ion mobilities suggest that these properties could be exploited to develop an extremely sensitive detector of electron attaching species.

6. G. Bakale, U. Sowada and W. F. Schmidt, "Electron Attachment to SF$_6$ in Nonpolar Liquids", J. Phys. Chem. 79, 3041 (1975).

The fact that the proposed detecting system responds only to electrophilic compounds (in picogram quantities), should now be combined with a statement from Bridges recent review of screening tests for carcinogens; viz "detecting DNA damage is merely a very sensitive way of detecting electrophilic reagents . . . " [7] This statement and the general conclusion that the DNA damaging ability of a compound is a measure of the compound's carcinogenicity clearly indicate the potential value of the proposed PEAC-LC system as a carcinogen monitor.

7. B. A. Bridges, "Short Term Screening Tests for Carcinogens", Nature 261, 195 (1976).

DEVELOPMENT OF PEAC-LC

The PEAC-LC system described herein uses several areas of research, viz chromatography, electron and ion current mensuration, and transport and attachment properties of quasifree electrons in nonpolar liquids and biological systems.

Figure 1:
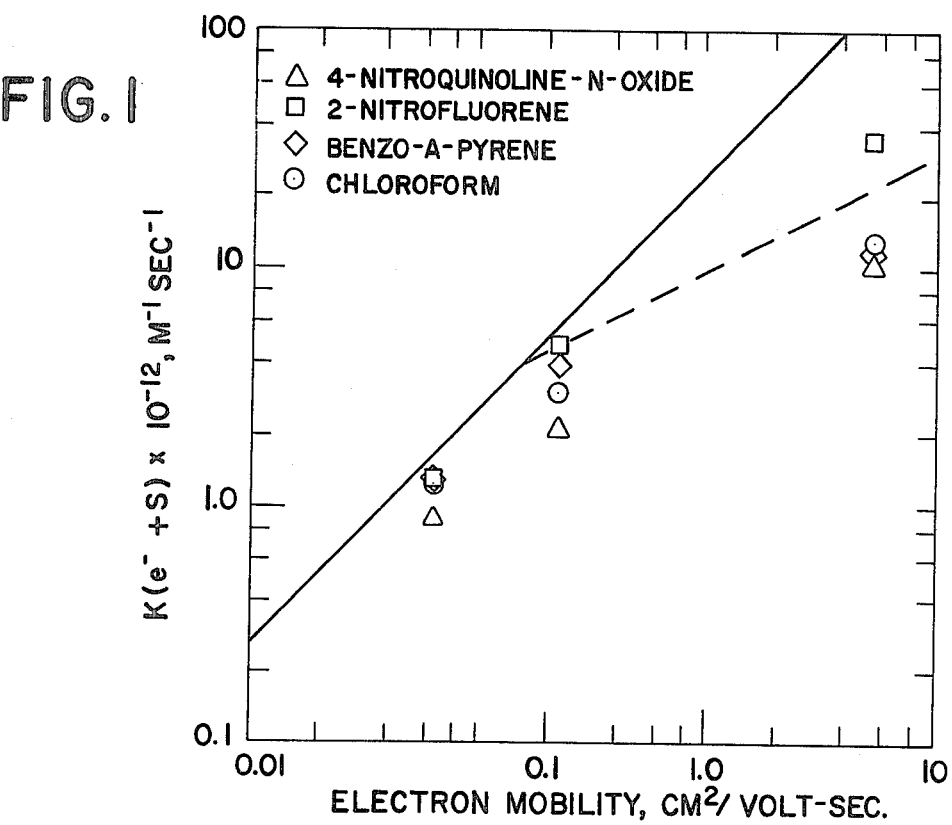
FIG. 1 shows the dependence of rate constant of electron attachment to carcinogens on the electron mobility in various solvents at 20° C.

The exploitation of the extremely high mobilities and attachment rates of quasifree electrons in nonpolar liquids is the key to this detection system. Preliminary results demonstrating the difference between electron attachment rates to biomolecules and carcinogens are shown in Tables I and II, respectively. The effect of different solvents on the attachment rates to four carcinogens is shown in FIG. 1. These data represent observations of the quasifree electron-accepting capacity of carcinogens.

Table I

| Rate constants of electron attachment to biomolecules in n-hexane at 20° C. | |
|---|---|
| Biomolecule | k × 10$^{-9}$, M$^{-1}$sec$^{-1}$ |
| indole | <0.5 |
| L-cystine | N.R.* |
| tetraglycine | N.R. |
| N-acetyl-L-tryptophan | N.R. |
| lecithin | <6 |
| cholesterol | <7 |
| amino benzene | <5 |
| water | <1 |

*N.R. denotes "no reaction"

Table II

| Rate constants of electron attachment to four classes of carcinogens in three non-polar solvents at 20° C. | | | |
|---|---|---|---|
| | k × 10$^{-12}$, M$^{-1}$sec$^{-1}$ in solvent: | | |
| Carcinogen | n-hexane | c-hexane | i-octane |
| benzo-α-pyrene | 1.3 | 4.0 | 12 |
| 2-nitrofluorene | 1.3 | 4.8 | 36 |
| 4-nitroquinoline-N-oxide | 0.9 | 2.1 | 10 |
| chloroform | 1.2 | 3.0 | 13 |

CONVENTIONAL HPLC

Figure 2:
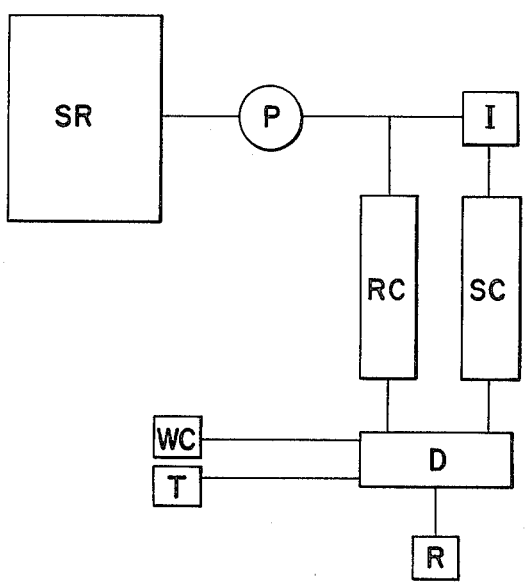
FIG. 2 shows a block diagram of conventional high pressure liquid chromatography system.

A block diagram of a typical HPLC system is presented in FIG. 2. The major components of this system are: a solvent reservoir (SR), a solvent pump (P), a sample injection port (I), a reference (RC) and a sample (SC) chromatograph column, a sample collection trap (T), a solvent waste collector (WC), a detector (D) and a recorder (R).

The sample is introduced to the LC carrier solvent through a valve system in the injection port where it mixes with the solvent which is pumped under a pressure of ~500–3,000 psi. The solution is then pumped to the chromatograph column where the components of the sample are separated due to their different physical or chemical interaction with the column substrate. Each component is separately eluted from the column by the continuously flowing solvent and when elution is complete, the components are carried by the solvent into the detector. At this point, the differential pressure gradient caused by the small diameter column packing is dissipated and the solution pressure is essentially atmospheric.

The response of the detector to the presence of the sample components generally is based upon a difference in a physical or chemical property of the solution compared to that of the pure solvent; e.g. refractive index (RI) or ultraviolet (UV) absorption are two of the most commonly used detection properties. The response from the detector is usually recorded on an x-t strip chart recorder. After passing through the detector, the solution is either discarded via WC, recycled for another pass through the system or diverted to a trap T, where it is collected for further analysis if desired. Each component in the sample can be separately collected and system pressures and column packings and temperatures can be varied to complete analyses in less than an hour for most samples.

Figure 3:
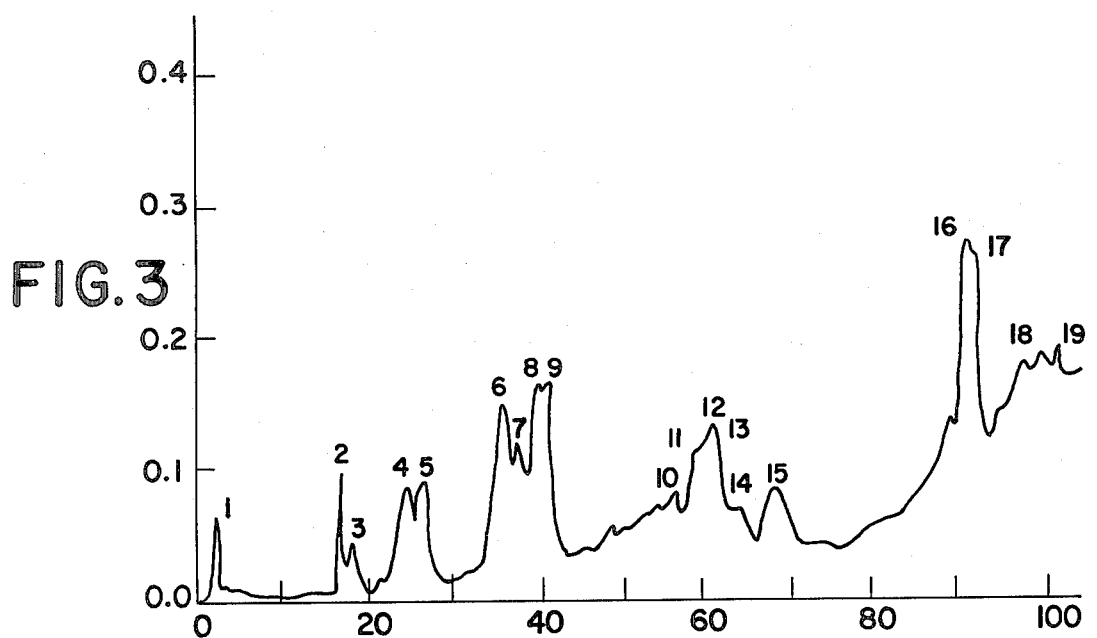
FIG. 3 shows the liquid chromatogram demonstrating separation of nineteen polycyclic aromatic hydrocarbons by HPLC.

A typical LC chromatogram reproduced from the work of Dong, Locke and Ferrand [8] is shown in FIG. 3 for the separation of nineteen polycyclic aromatic hydrocarbons. Of the nineteen, at least one component, benzo-α-pyrene, is recognized as a carcinogen and our present pulsed conductivity studies indicate that several of the other components are also carcinogens. The sample Dong et al used in this study was the particulate matter in New York City air. If the same sample were analyzed in the proposed PEAC-LC system, a chromatogram similar to FIG. 3 would result but with the omission of peaks from the non-carcinogenic components.

8. M. Dong, D. C. Locke and E. Ferrand, "High Pressure Liquid Chromatographic Method for Routine Analysis of Major Parent Polycyclic Aromatic Hydrocarbons in Suspended Particulate Matter", Anal. Chem 48, 368 (1976).

THE PEAC DETECTOR

Figure 4:
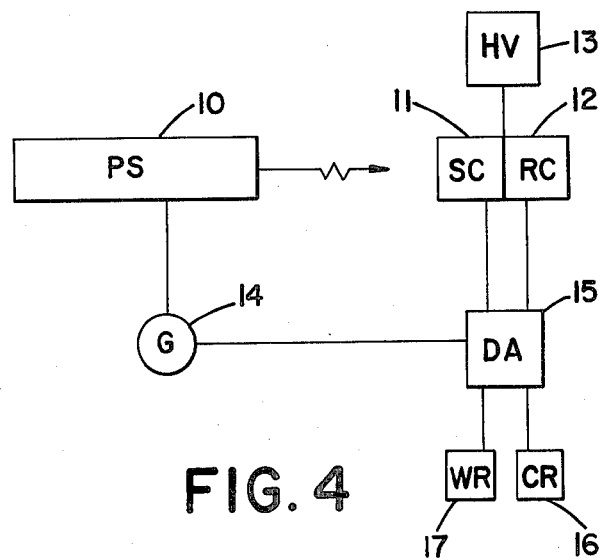
FIG. 4 shows a block diagram of a PEAC detector.

A schematic diagram of our PEAC detector is shown in FIG. 4. A pulsed source 10 (PS) of ionizing radiation produces quasifree electrons in the sample-effluent solution as its flows through the parallel plate ionization chamber 11 (SC). A second ionization chamber having identical geometry to SC is also irradiated by PS, but in this reference chamber 12 (RC) only pure solvent flows. Either a DC or high frequency AC electric field is maintained across both chambers with the potential supplied by the high voltage power supply 13 (HV). The current produced by the charge-carriers moving in the fields across RC and SC following a pulse of irradiation is gated 14 at a predetermined time after the pulse to a differential amplifier 15 (DA). The gate is closed at a prescribed time after the pulse at which all of the charge-carriers have been neutralized either at the electrodes or by recombination. After gating and amplification, the differential signal is recorded on either an x-t strip chart recorder 16 (CR) or a waveform recorder 17 (WR).

When neutralization is complete, the entire cycle is repeated beginning with another irradiation pulse of negligible width compared to the time required for electrons to drift to the electrodes and concluding with recording the ion current differential signal resulting from sampling the fresh effluent that has flowed into the ion chambers. This process is repeated continually (20 cps for the example given below) and the time constant of the amplifier-recorder system is chosen to be sufficiently long to produce a smoothed read-out of the differential current.

Typical specifications of the main detector components are as follows: (1) iso-octane-filled ion chambers with 1 cm$^2$ electrodes separated 1 mm with a potential of +2,000 volts applied to the anodes, (2) irradiation of the ion chambers by a 20 pulse/second train of submillisecond pulses of 0.15 rad each produced by either a pulsed particle accelerator or by intermittent exposure to a naturally decaying radioactive source, and (3) an amplification and recorder system to monitor the 40 nanoamp ion currents produced in the sample and reference ion chambers. When an electrophilic solute flows into the sample chamber, the ion current in the sample chamber will be greater than the 40 nanoamp "background" level and this differential current is the recorded output. With these conditions, space charge effects and chargecarrier recombination would be negligible. [9,10]

9. E. C. Gregg and G. Bakale, "Ionization Currents in Liquid Ionization Chambers: Low Conductivity Liquids", Rad. Res. 42, 13 (1970).
10. G. Bakale, E. C. Gregg and R. D. McCreary, "Decay of Quasifree Electrons in Pulse-Irradiated Hydrocarbons", J. Chem. Phys. 57, 4246 (1972).

Figure 5:
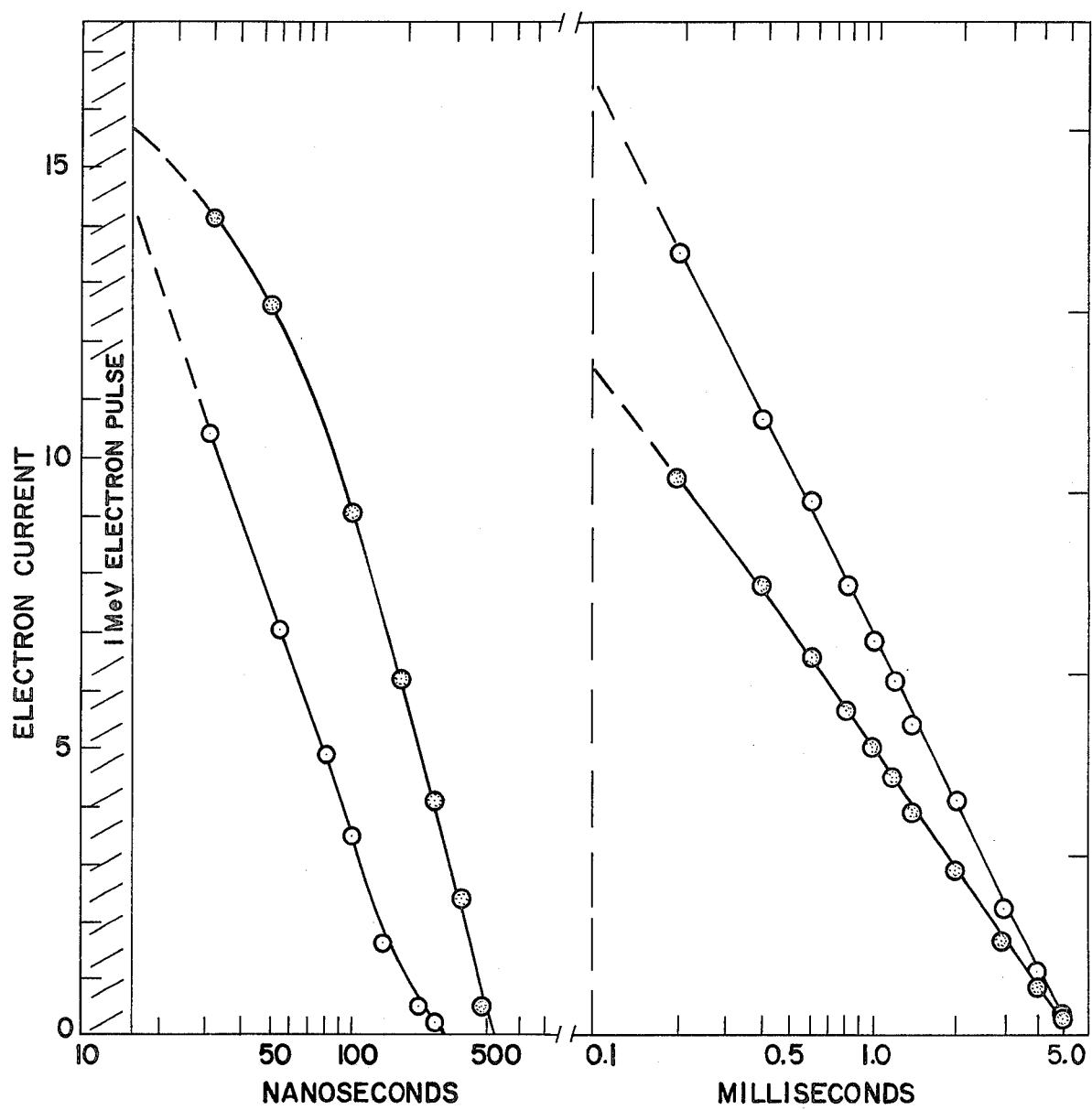
FIG. 5 shows the decay of electron (A) and ion (B) currents following irradiation of "pure" iso-octane (◎) and a 0.33 micromolar solution of 2-nitrofluorene in iso-octane ( ◯ ) at 20° C. by a 1 rad dose from a 16 nanosecond pulse of 1 MeV electrons with 3,000 volts applied across 0.71 cm$^2$ electrodes separated 0.06 cm.

The increase in the ion current in the sample chamber occurring when an electron-accepting solute is present is due to the conversion of high mobility ($\mu_e \simeq 5$ cm$^2$ volt sec) quasifree electrons attaching to the solute before being neutralized at the anode and, as a result of this attachment, being converted to sluggish, low mobility ($\mu < 10^{-3}$ cm$^2$ volt sec) anions. This decrease in the sample chamber electron current and subsequent increase in the ion current due to the present of an electron-acceptor converting electrons to anions is illustrated in FIG. 5 which presents our data of electron attachment to the carcinogen 2-nitrofluorene.

The sensitivity of a PEAC detector filled with iso-octane for the ion chambers and irradiation conditions specified is as follows: The transit time of electrons with $\mu_e = 5.5$ cm$^2$/volt sec across the 1 mm inter-electrode distance with +2,000 volts applied to the anode is 0.91 microseconds. In order for a detectable imbalance between the sample and reference chambers to occur, approximately five percent of these electrons must be converted to anions by an electrophilic solute before drifting to the anode. For a solute such as 2-nitrofluorene which attaches quasifree electrons with a rate constant of $3.6 \times 10^{13} M^{-1} sec^{-1}$ (Table II), 21 nanomoles/liter attach half of the electrons in 0.91 microseconds or 2.1 nanomoles/liter attach five percent of the electrons in the same time. The ion chamber volume is 0.1 cm$^3$ and the quantity of nitrofluorene causing this five percent imbalance of the PEAC ion chambers is 0.21 picomoles or 44 picograms.

ANALYSIS BY PEAC-LC

The PEAC-LC is for both qualitative and quantative analysis as shown by the following example. A smokestack gas tested for carcinogenic polycyclic aromatic hydrocarbons (PAH's), would have a measured volume of the gas bubbled through the solvent in the PEAC-LC. Column packings, flow rates and other chromatographic conditions are chosen to resolve the suspected PAH's and produce a chromatogram similar to that shown in FIG. 3. An aliquot of the sample is injected in the LC and when the PEAC detector responded, the retention time of the component producing the signal imbalance is compared with known retention times of PAH's eluted under the same chromatographic conditions. Thus, identification would be made by matching sample retention times with known standards. Alternatively, the unknown could be trapped after elution from the PEAC-LC and identified by a secondary analytical technique such as UV, IR or GC-MS. Knowledge of both the identity and the electron attachment rate constant of the PAH's permits evaluation of the concentration of each PAH in the smokestack gas.

Once a specific PAH is identified as present in the gas, the chromatographic conditions are modified to reduce the analysis time in order to optimize the frequency of sampling the gas. For example, if only benzo-α-pyrene is detected in the sample at 70 minutes (see FIG. 3), the column packing and length and flow rate are changed to reduce the retention time and permit hourly samplings of the gas. Such monitoring would be preferred to conventional carcinogen screening tests which require days.

SOLVENT PURIFICATION

The exceedingly high reactivity of quasifree electrons necessitates the use of extremely pure solvents in the PEAC-LC system. These same requirements of solvent purity exist for our pulsed conductivity studies of electron attachment rates in non-polar liquids and has resulted in our developing purification techniques capable of producing liter quantities of solvent per day in which quasifree electrons can be studied. Our purification technique differs from that developed in other laboratories making similar studies in that our technique does not use: (1) high vacuum technology, which limits solvent production rate, (2) dangerous reactants such as sodium or potassium, which present an extreme flammability and explosion hazard, nor (3) research grade solvents, which are approximately ten times as expensive as the grade of solvents used in our studies and, if used, would make routine PEAC-LC extremely expensive.

In our technique, Fisher "99 mol percent" grade n-hexane, c-hexane or iso-octane is used as the starting solvent and about 500 ml of the liquid is placed in a glass apparatus designed to permit a stream of Matheson Ultra-High Purity argon (99.999 mol%) to be bubbled through the solvent and to prevent atmospheric contamination once the argon purge is begun. After ten minutes of argon bubbling, the solvent is passed over a 1.2 cm $\times$ 1 m column of a mixture of Molecular Sieve 4A and silica gel which had been activated at 500° C. and then maintained under an argon atmosphere while cooled to room temperature before the solvent was passed through it. The first 300 ml of solvent eluting from the column is collected in a specially designed flask which is also purged with argon, and the collected solvent is again bubbled with argon before being irradiated with a dose of $\sim 10^5$ rads of cobalt-60 gamma radiation. The purpose of this step is to produce electrons in the liquid which react with electron-attaching impurities in the solvent and thereby form anions that apparently undergo recombination or wall reactions and are thus converted to less electrophilic molecules. The solvent is then admitted to an argon purged ionization chamber and again bubbled with argon before the electron half-life in the liquid is measured. Electron half-lives of 1500, 900 and 300 nsec in n-hexane, c-hexane and iso-octane, respectively, are routinely obtained using this technique.

An estimate of the concentration of electron-attaching impurities remaining in the solvents after the above purification steps can be made from the measured electron half-lives and the rate constants listed in Tables I and II. For an inefficient electron acceptor such as aniline (amino benzene) for which the electron attachment rate constant is $<5 \times 10^9 M^1 sec^{-1}$ in n-hexane, the concentration of adventitious aniline required to produce an electron half-life of 1500 nsec in n-hexane is $>92$ micromolar. This is in contrast to an efficient carcinogen impurity such as 2-nitrofluorene for which the attachment rate constant is $3.6 \times 10^{13} M^{-1} sec^{-1}$ in iso-octane and, therefore, a concentration of only 13 nanomolar or 2 parts per billion (mol/mol) would reduce the electron half-life to 1500 nanosec in iso-octane.

What is claimed is:

1. A method of determining the electron attachment rate of an unknown electrophilic compound by a pulsed conductivity technique which comprises:
    (a) dissolving the unknown compound in a nonpolar solvent;
    (b) passing the solvent containing the unknown compound in a sample compartment of a dual compartment ionization chamber with the other compartment containing a reference standard consisting of the same nonpolar solvent without the unknown compound, and each compartment having a set of collecting electrodes;
    (c) irradiating the dual compartment ionization chamber with ionizing radiation to produce quasifree electrons in the nonpolar solvents in each compartment;
    (d) connecting both sets of ionization chamber electrodes to an electronic measuring device; and
    (e) measuring and recording as a function of time the difference between the current from the compartments containing the reference standard and the unknown compound to determine the electron attachment rate of the latter.

2. A method of distinguishing carcinogenicity in electrophilic compounds by measuring the extremely high attachment rates of quasifree electrons to the unknown sample in nonpolar solvents, which comprises:
    (a) dissolving the unknown compound in a nonpolar solvent;
    (b) passing the solvent containing the unknown compound in a sample compartment of a dual compartment ionization chamber with the other compartment containing a reference standard consisting of the same nonpolar solvent without the unknown compound, and each compartment having a set of collecting electrodes;
    (c) irradiating the dual compartment ionization chamber with ionizing radiation to produce quasifree electrons in the nonpolar solvents in each compartment;
    (d) connecting both sets of ionization chamber electrodes to an electronic measuring device; and
    (e) measuring and recording as a function of time the difference between the current from the compartments containing the reference standard and the unknown compound to determine the electron attachment rate of the latter.

3. The method of determining the electron attachment rate of an unknown electrophilic compound, which comprises:
  (a) separating and identifying the compound with high pressure liquid chromatography;
  (b) passing the solvent containing the unknown compound in a sample compartment of a dual compartment ionization chamber with the other compartment containing a reference standard consisting of the same nonpolar solvent without the unknown compound, and each compartment having a set of collecting electrodes;
  (c) irradiating the dual compartment ionization chamber with ionizing radiation to produce quasifree electrons in the nonpolar solvents in each compartment;
  (d) connecting both sets of ionization chamber electrodes to an electronic measuring device; and
  (e) measuring and recording as a function of time the difference between the current from the compartments containing the reference standard and the unknown compound to determine the electron attachment rate of the latter.

4. The method of claim 1, in which the ionizing radiation is delivered in a pulse of less than 1 millisecond duration.

5. The method of claim 1, in which the ionizing radiation is delivered in a pulse of approximately 10 nanoseconds duration.

6. The method of claim 1, in which the nonpolar solvent has less than 1 ppm of electron-attaching impurity.

7. A method of screening unknowns for carcinogenicity which comprises:
  (a) dissolving an unknown compound in a nonpolar solvent;
  (b) passing the solution containing the unknown compound in an ionization chamber;
  (c) irradiating the solvent with pulsed ionizing radiation to produce quasifree electrons therein; and
  (d) measuring the magnitude and the decay rate of the current produced in the ionization chamber containing the unknown compound dissolved in the nonpolar solvent.

8. The method of claim 7, in which the ionizing radiation is delivered in a pulse of less than 1 millisecond duration.

9. The method of claim 7, in which the ionizing radiation is delivered in a pulse of approximately 10 nanoseconds duration.

10. The method of claim 7, in which the nonpolar solvent has less than 1 ppm of electron-attaching impurity.

* * * * *